(12) United States Patent
Al-Sadah et al.

(10) Patent No.: US 8,129,701 B2
(45) Date of Patent: Mar. 6, 2012

(54) AREAL MODULATOR FOR INTENSITY MODULATED RADIATION THERAPY

(76) Inventors: Jihad H. Al-Sadah, Madison, WI (US);
David C. Westerly, Madison, WI (US);
Patrick M. Hill, Madison, WI (US);
Thomas R. Mackie, Verona, WI (US)

( * ) Notice: Subject to any disclaimer, the term of this patent is extended or adjusted under 35 U.S.C. 154(b) by 536 days.

(21) Appl. No.: 12/038,659

(22) Filed: Feb. 27, 2008

(65) Prior Publication Data
US 2008/0260098 A1 Oct. 23, 2008

Related U.S. Application Data

(60) Provisional application No. 60/891,859, filed on Feb. 27, 2007.

(51) Int. Cl.
*A61N 5/00* (2006.01)
(52) U.S. Cl. .............. 250/505.1; 250/491.1; 250/492.1; 250/515.1; 250/503.1; 250/493.1; 359/237; 378/65
(58) Field of Classification Search .............. 250/491.1, 250/492.1, 505.1, 515.1, 503.1, 493.1; 378/65; 359/237
See application file for complete search history.

(56) References Cited

U.S. PATENT DOCUMENTS

| | | | |
|---|---|---|---|
| 4,027,167 A * | 5/1977 | Pollermann | 378/153 |
| 4,276,477 A | 6/1981 | Enge | |
| 5,165,106 A * | 11/1992 | Barthelmes et al. | 250/505.1 |
| 5,192,869 A * | 3/1993 | Kumakhov | 250/505.1 |
| 5,317,616 A | 5/1994 | Swerdloff et al. | |
| 5,394,452 A | 2/1995 | Swerdloff et al. | |
| 5,442,675 A | 8/1995 | Swerdloff et al. | |
| 5,528,650 A | 6/1996 | Swerdloff et al. | |
| 5,548,627 A | 8/1996 | Swerdloff et al. | |
| 5,625,663 A | 4/1997 | Swerdloff et al. | |
| 5,661,773 A | 8/1997 | Swerdloff et al. | |
| 5,668,371 A * | 9/1997 | Deasy et al. | 850/1 |
| 5,673,300 A | 9/1997 | Reckwerdt et al. | |
| 5,724,400 A | 3/1998 | Swerdloff et al. | |
| 5,802,136 A | 9/1998 | Carol | |
| 5,991,362 A * | 11/1999 | Jones | 378/152 |
| 6,188,749 B1 * | 2/2001 | Schiller et al. | 378/158 |
| 6,345,114 B1 | 2/2002 | Mackie et al. | |
| 6,385,286 B1 | 5/2002 | Fitchard et al. | |
| 6,438,202 B1 | 8/2002 | Olivera et al. | |

(Continued)

FOREIGN PATENT DOCUMENTS

DE 19907098 A1 8/2000

(Continued)

OTHER PUBLICATIONS

Watanabe T and Kuwano H. A microvalve matrix using piezoelectric actuators, Microsystem Technologies 107-111, 1997.*

(Continued)

*Primary Examiner* — Phillip A Johnston
*Assistant Examiner* — Michael J Logie
(74) *Attorney, Agent, or Firm* — Boyle Fredrickson, S.C.

(57) ABSTRACT

A modulator for radiation therapy provides modulation of an area beam to decrease treatment time. Separate channels passing modulated "beamlets" are possible by spacing the channels such that spreading of the beams and multiple angles of treatment eliminate cold spots. The space between the channels allows well-defined channel walls and space for modulator mechanisms.

19 Claims, 4 Drawing Sheets

U.S. PATENT DOCUMENTS

| | | | |
|---|---|---|---|
| 6,453,013 B2* | 9/2002 | Prins | 378/158 |
| 6,560,311 B1 | 5/2003 | Shepherd et al. | |
| 6,618,467 B1 | 9/2003 | Ruchala | |
| 6,636,622 B2 | 10/2003 | Mackie et al. | |
| 6,661,870 B2 | 12/2003 | Kapatoes et al. | |
| 6,731,970 B2 | 5/2004 | Scholssbauer et al. | |
| 6,915,005 B1 | 7/2005 | Ruchala et al. | |
| 7,046,831 B2 | 5/2006 | Ruchala et al. | |
| 7,186,986 B2 | 3/2007 | Hinderer et al. | |
| 7,207,715 B2 | 4/2007 | Yue | |
| 7,302,038 B2 | 11/2007 | Mackie | |
| 7,400,434 B2* | 7/2008 | Brahme et al. | 359/237 |
| 2002/0136439 A1 | 9/2002 | Ruchala et al. | |
| 2003/0160189 A1 | 8/2003 | Matsuda | |
| 2003/0198319 A1 | 10/2003 | Toth et al. | |
| 2005/0123092 A1 | 6/2005 | Mistretta et al. | |
| 2005/0197564 A1 | 9/2005 | Dempsy | |
| 2006/0193441 A1* | 8/2006 | Cadman | 378/153 |
| 2006/0226372 A1 | 10/2006 | Yanagisawa | |
| 2006/0285639 A1 | 12/2006 | Olivera et al. | |
| 2007/0029510 A1 | 2/2007 | Hermann | |
| 2007/0036267 A1 | 2/2007 | Becker et al. | |
| 2007/0040127 A1* | 2/2007 | Brahme et al. | 250/389 |
| 2007/0041494 A1 | 2/2007 | Ruchala et al. | |
| 2007/0041495 A1 | 2/2007 | Olivera et al. | |
| 2007/0041496 A1 | 2/2007 | Olivera et al. | |
| 2007/0041497 A1 | 2/2007 | Schnarr et al. | |
| 2007/0041498 A1 | 2/2007 | Olivera et al. | |
| 2007/0041499 A1 | 2/2007 | Lu et al. | |
| 2007/0041500 A1 | 2/2007 | Olivera et al. | |
| 2007/0043286 A1 | 2/2007 | Lu et al. | |
| 2007/0076846 A1 | 4/2007 | Ruchala et al. | |
| 2007/0104316 A1 | 5/2007 | Ruchala et al. | |
| 2007/0195922 A1 | 8/2007 | Mackie et al. | |
| 2007/0195929 A1 | 8/2007 | Ruchala et al. | |
| 2007/0195930 A1 | 8/2007 | Kapatoes et al. | |
| 2007/0242801 A1 | 10/2007 | Mackie et al. | |

FOREIGN PATENT DOCUMENTS

| | | |
|---|---|---|
| EP | 0986070 A | 3/2000 |
| EP | 1045399 A | 10/2000 |
| JP | 2000 214298 A | 8/2000 |
| WO | WO02/07817 A | 1/2002 |
| WO | WO02/41948 A | 5/2002 |
| WO | WO2005/004168 A | 1/2005 |
| WO | WO2007/021226 A | 2/2007 |

OTHER PUBLICATIONS

International Search Report, PCT Application No. PCT/US2008/055104, dated Jul. 17, 2008, ISA/EPO, 2280 HV Rijswijk, NL.
International Search Report, PCT Application No. PCT/US2008/055070, dated Jul. 17, 2008, ISA/EPO, 2280 HV Rijswijk, NL.
International Search Report, PCT Application No. PCT/US2008/055069, dated Jul. 17, 2008, ISA/EPO, 2280 HV Rijswijk, NL.
International Search Report, PCT Application No. PCT/US2008/055161, dated Jul. 17, 2008, ISA/EPO, 2280 HV Rijswijk, NL.
International Search Report, PCT Application No. PCT/US2008/055083, dated Jul. 17, 2008, ISA/EPO, 2280 HV Rijswijk, NL.
International Search Report, PCT Application No. PCT/US2008/055096 dated Jul. 17, 2008, ISA/EPO, 2280 HV Rijswijk, NL.
International Search Report, PCT Application No. PCT/US2008/055090 dated Jul. 17, 2008, ISA/EPO, 2280 HV Rijswijk, NL.
International Search Report, PCT Application No. PCT/US2008/055147, dated Jul. 25, 2008, ISA/EPO, 2280 HV Rijswijk, NL.

Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.
Deasy, JO, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos. California. USA.
Deasy, JO, A proton dose calculation algorithm for conformal therapy simulations based on Moliere theory of lateral deflections, Med. Phys., Apr. 1998, 25:476-483, American Association of Physical Medicine, New York, New York.
Lomax, AJ, Intensity modulation methods for proton radiotherapy, Phys. Med. Biol., 1999 44:185-205, IOP Publishing Ltd., Bristol, UK.
Lomax, AJ, et al. Intensity modulated proton therapy: A clinical example, Mar. 2001, Med. Phys. 28:317-324, American Association of Physical Medicine, New York, New York.
Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.
Lomax, AJ, et al., Treatment planning and verification of proton therapy using spot scanning: initial experiences. 2004a, Med. Phys. 31:3150-3157, American Association of Physical Medicine, New York, New York.
Lomax, AJ, et al., The clinical potential of intensity modulated proton therapy, 2004b, Z. Med. Phys. 14:147-152, Elsevier, Amsterdam, Netherlands.
Kanai, T, et al., Spot scanning system for proton radiotherapy, Jul./Aug. 1980, Med. Phys 7:365-369, American Association of Physical Medicine, New York, New York.
Moyers MF, (Proton therapy, Van Dyk (ed), The Modern Technology of Radiation Oncology, 1999, pp. 823-869, Medical Physics Publishing, Madison, WI.
Nill, S, et al., Inverse planning of intensity modulated proton therapy, 2004, Z Med. Phys. 14:35-40, Elsevier, Amsterdam, Netherlands.
Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.
Paganetti H, Proton Therapy: A Workshop Handout. 2005, Private Communication, Massachusetts General Hospital, Boston, MA.
Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.
Wilson RW., Radiological use of fast protons. Nov. 1946, Radiology 47:487-491, Radiological Society of North America, Easton, Pennsylvania.
Yu C., Intensity modulated arc therapy with dynamic multileaf collimation: an alternative to tomotherapy, 1995, Phys. Med. Biol. 40:1435-1449, IOP Publishing Ltd., Bristol, UK.
Anderov V., Combined X-Y scanning magnet for conformal proton radiation therapy, Med. Phys., Mar. 2005, 32:815-818, American Association of Physical Medicine, New York, New York.
Goitlein, M., Beam scanning for heavy charged particle radiotherapy, Nov./Dec. 1983, Med. Phys. 10 (6) pp. 831-840, American Association of Physical Medicine, New York, New York.

* cited by examiner

AREAL MODULATOR FOR INTENSITY MODULATED RADIATION THERAPY

CROSS-REFERENCE TO RELATED APPLICATIONS

This application claims the benefit of U.S. Provisional Application 60/891,859, filed Feb. 27, 2007, the disclosure of which is incorporated herein by reference.

STATEMENT REGARDING FEDERALLY SPONSORED RESEARCH OR DEVELOPMENT

This invention was made with government support under CA088960 awarded by the National Institutes of Health. The government has certain rights in the invention.

BACKGROUND OF THE INVENTION

The present invention relates to radiation therapy systems for the treatment of cancer and the like and, in particular, to a system providing improved treatment speed and accuracy.

External beam radiation therapy may treat a tumor within the patient by directing high-energy radiation in one or more beams toward the tumor. Recent advanced external beam radiation systems, for example, as manufactured by Tomotherapy, Inc., treat a tumor with multiple x-ray fan beams directed at the patient over an angular range of 360°. Each of the beams is comprised of individually modulated beamlets whose intensities can be controlled so that the combined effect of the beamlets, over the range of angles, allows an arbitrarily complex treatment area to be defined.

X-rays deposit energy in tissue along the entire path between the x-ray source and the exit point in the patient. While judicious selection of the angles and intensities of the x-ray beamlets can minimize radiation applied to healthy tissue outside of the tumor, inevitability of irradiating healthy tissue along the path to the tumor has suggested the use of ions such as protons as a substitute for x-ray radiation. Unlike x-rays, protons may be controlled to stop within the tissue, reducing or eliminating exit dose through healthy tissue on the far side of the tumor. Further, the dose deposited by a proton beam is not uniform along the entrance path of the beam, but rises substantially to a "Bragg peak" near a point where the proton beam stops within the tissue. The placement of Bragg peaks inside the tumor allows for improved sparing of normal tissue for proton treatments relative to x-ray treatments.

Current proton therapy systems adopt one of two general approaches. In the first approach, the proton beam is expanded to subtend the entire tumor and the energy of the protons, and hence their stopping point in the tissue, is spread in range, to roughly match the tumor depth. Precise shaping of the exposure volume is provided by a specially constructed range correction compensator which provides additional range shifting to conform the distal edge of the beam to the distal edge of the tumor. This treatment approach essentially treats the entire tumor at once and, thus, is fast and yet less precise and requires the construction of special compensators for each treatment field.

In a second approach, termed the "magnetic spot scanning" (MSS) approach, the proton beam remains narrowly collimated in a "pencil beam" and is steered in angle and modulated in range to deposit the dose as a series of small spots within the patient. The spots are located to cover the tumor in successive exposures until an arbitrary tumor volume has been irradiated. This approach is potentially very accurate, but because the tumor is treated in many successive exposures, this approach is much slower than the SOBP approach. Further the small spot sizes create the risk of uneven dose placement or "cold spots" between the treatment spots, something that is exacerbated if there is any patient movement between exposures.

The benefits of both of these techniques, without the drawbacks, might be obtained if it were possible to produce an areal beam composed of individually modulated pencil beams. Producing a treatment beam of this type would require an areal modulator capable of receiving the areal beam and separately modulating small rays within the beam.

An areal modulator intended for x-ray radiation is described in U.S. Pat. No. 5,802,136 to Carol entitled: "Method and Apparatus For Conformal Radiation Therapy" issued Sep. 1, 1998 and hereby incorporated by reference. This modulator employs a chamber positioned within the beam and holding a pool of mercury. Within the mercury are axially extending balloons loosely stabilized by radiolucent pins. When the balloons are deflated, radiation along the beam axis is blocked by the mercury. When the balloons are inflated, each balloon provides a separate channel allowing passage of the radiation. The balloons may be individually inflated and deflated and each deflated balloon is extremely thin and deflates to an undulating membrane so as to prevent leakage of radiation through the deflated balloon (hotspots). Further, the balloons, when fully inflated, may effectively displace mercury between them eliminating cold spots as might be obtained were the balloons separated by rigid radio-opaque walls.

Mercury is relatively heavy and toxic and the accurate control of loosely constrained, flexible balloons in a bath of mercury is a difficult engineering problem. Possibly for this reason, Carol also describes an embodiment in which the balloons are arranged in rigid compartments arranged in "checkerboard" fashion, with a balloon in every other cell of the checkerboard and the remaining cells being radio-opaque. The cold spots generated by the radio-opaque cells are dealt with by making two successive exposures of the patient with the checkerboard shifted appropriately between the exposures, for example, rotated about its axis or used to expose the patient from the opposite side of the patient after rotating about the patient. In this way the opaque cells and the cells with the balloons switch places to provide for complete exposure.

BRIEF DESCRIPTION OF THE PREFERRED EMBODIMENT

The present inventors have determined that, particularly for proton radiation, the spreading of the beam after modulation permits the significant separation of radiating modulating channels of an areal modulator without creating significant cold spots. This spacing is sufficient to permit dimensionally accurate channel walls, for example, to permit modulation by changing a height of a column of liquid capped with a piston and/or the use of more shutter systems using rotating elements that necessarily leave gaps between them. The spacing of the channels also allows actuating mechanisms and sensors to be located adjacent to the attenuation elements in the channel walls.

Specifically then, the present invention provides a radiation therapy machine having a patient support and a source of a radiation providing an area beam directed toward a patient to expose tissue of the patient supported by the patient support. An areal modulator is position between the source of radiation and the patient support and includes a radio-opaque plate extending over an area of the area beam and having a plurality of channels within the area dispersed in two dimensions for passing radiation, the portion of the radio-opaque plate outside of the channels blocking passage of the radiation. Each of the channels includes attenuation elements, located in the channels, to independently attenuate radiation passing through the channels. The channels are spaced with respect to each other so that divergence of the radiation after passing through the radio-opaque plate permits substantially uniform exposure of the tissue of the patient over an area corresponding to the area of the radio-opaque plate holding the channels.

Thus, it is one object of an embodiment of the invention to provide for improved treatment speed in radiotherapy by parallel modulation of different portions of an area beam as opposed to a single pencil. It is yet another object of an embodiment of the invention to provide an improved modulator mechanism enabled by the possibility of separating the attenuating channels by an opaque matrix while still permitting a substantially uniform exposure of an area.

The device may be disposed within a gantry that is moved through a plurality of gantry angles during a radiation therapy session, and may further include a controller that independently controls the attenuation through each of the channels as a function of gantry angle.

It is thus an object of an embodiment of the invention to permit motion of the modulation assembly to further smooth the application of radiation provided by the separated attenuation channels.

The attenuation elements may be cylinders extending along an axis of the channels to hold attenuating fluid and connected to at least one valve system configured to adjust a height of attenuating fluid along the axis to continuously vary radiation passing through the channels.

It is thus an object of an embodiment of the invention to provide for uniform attenuation of the radiation beam within each channel. By providing a truly cylindrical column of liquid, all of the radiation passing through the chamber may be given the same attenuation, useful for precise control of the distal edge of Bragg peaks in proton radiation therapy.

The cylinders may include a floating piston defining a boundary between the attenuating fluid and a second non-attenuating fluid.

It is thus another object of an embodiment of the invention to provide a simple way of controlling the dimensions of a fluid material at various orientations of the modulator.

The attenuating fluid maybe selected from the group consisting of oil and water.

It is thus another object of an embodiment of the invention to eliminate the need to deal with problematic mercury.

Each cylinder may connect to at least two valves, one connected to a high-pressure reservoir to fill the cylinder and one connected to a low-pressure reservoir to empty the cylinder.

It is thus an object of an embodiment of the invention to provide for a method of rapid control of fluid heights by both actively filling and draining the cylinders.

The device may further include sensors for sensing the height of the piston and providing electrical signal to a control system for regulating the height of the fluid in the cylinder.

It is thus an object of an embodiment of the invention to provide extremely precise control of fluid heights.

As the gantry is moved through a plurality of gantry angles during a radiation therapy session, a controller may control the height of the attenuating fluid along the axis to vary continuously as a function of gantry angle.

It is thus an object of an embodiment of the invention to provide a treatment protocol that accommodates the continuous but speed-limited control of the beams attendant to filling and emptying cylinders with fluid. This control protocol takes advantage of the relative continuity of attenuation as a function of angle in a typical radiation treatment plan.

In an alternative embodiment, the attenuation elements may be shutters providing a variable blocking of the channels to continuously vary radiation passing through the channels.

It is thus an object of an embodiment of the invention to provide for a compact and fast acting mechanical attenuation mechanism.

The shutters may variably block the channels by changing an amount of overlap between different shutter elements.

It is thus an object of an embodiment of the invention to provide for shutter system that may be wholly contained within a channel and thus may be opened and closed without moving into the space of adjacent channels.

The shutter elements may be disks rotating about a common axis centered within the channel having cutouts that move into and out of alignment with rotation of the disks.

It is thus an object of an embodiment of the invention to provide for a mechanical mechanism that may be simply and reliably controlled.

These particular features and advantages may apply to only some embodiments falling within the claims and thus do not define the scope of the invention.

DETAILED DESCRIPTION OF THE DRAWINGS

Figure 1:
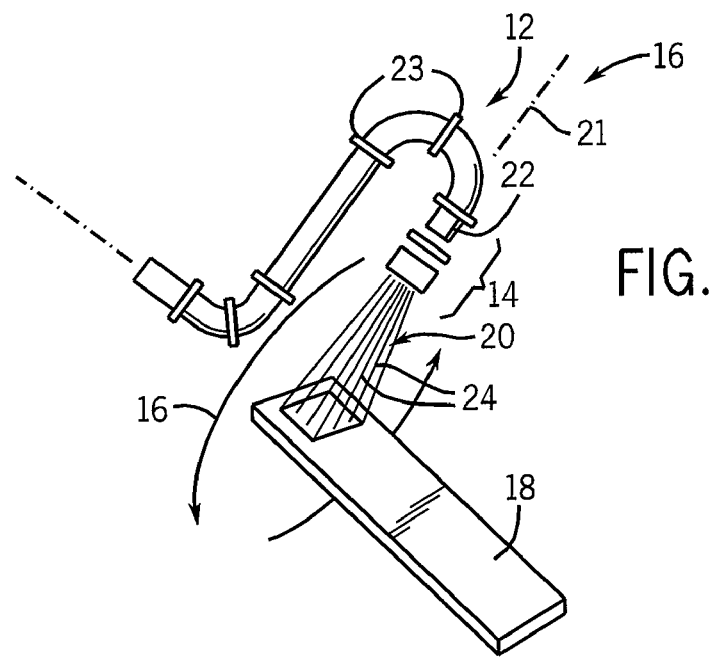
FIG. 1 is a simplified representation of a proton therapy machine suitable for use with the present invention and having a rotating gantry for directing an area beam of protons toward a patient support at a range of angles, the beamlets of the area beam controlled by an areal modulator.

Referring now to FIG. 1, a proton therapy machine 10 may include a gantry 12 having a treatment head 14 that may orbit 16 about a patient (not shown) on a patient support table 18. The treatment head 14 receives a source of protons from a proton source conduit 22 that may conduct protons from a synchrotron, cyclotron, or the like, and by means of bending magnets 23 direct them toward the patient support table 18 at all positions within the orbit 16. The protons from the proton source conduit 22 are received by the treatment head 14 which spreads the pencil beam into an area beam 20 extending along an axis 21, and individually modulates beamlets 24 within the area beam 20 in energy and intensity.

Figure 2:
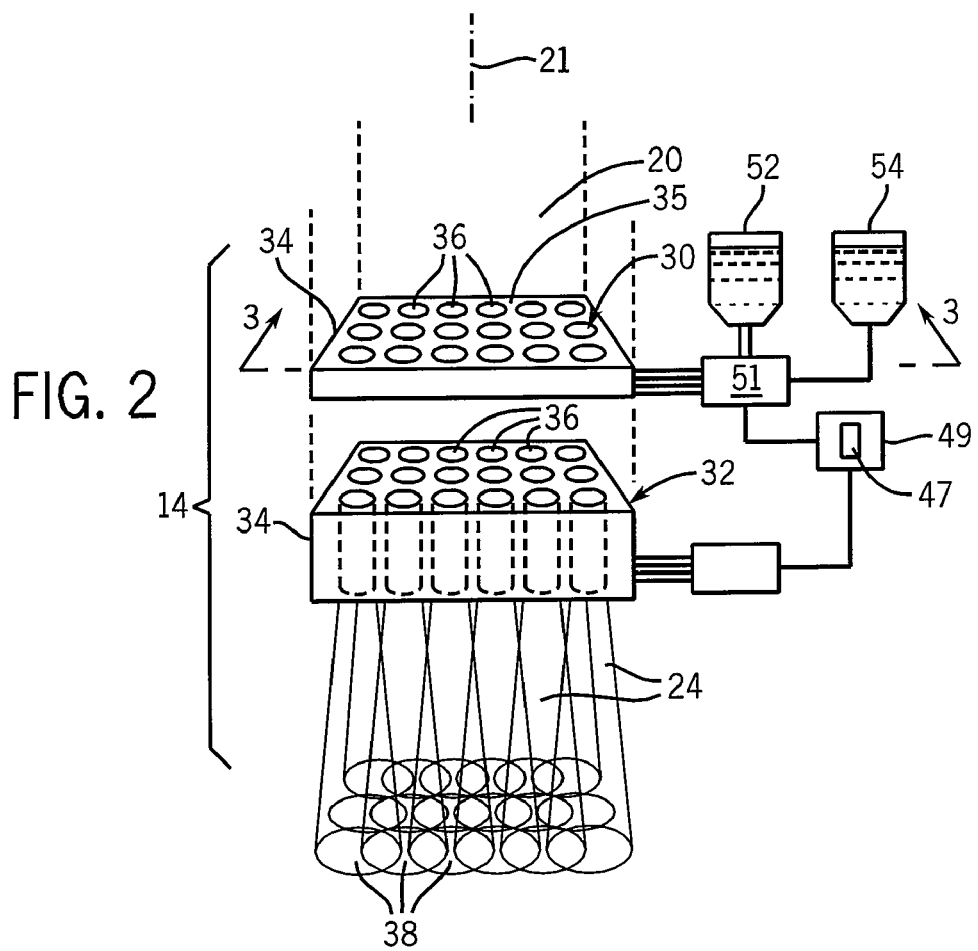
FIG. 2 is an exploded view of the areal modulator of FIG. 1 providing energy and intensity modulation.

Referring now to FIG. 2, the treatment head 14 includes a first energy modulator 30 and a second intensity modulator 32. Each modulator 30 and 32 comprises a radio-opaque plate 34 having a plurality of channels 36 cut therethrough that pass the area beam 20 as individual beamlets 24 separated over the area of the area beam 20 in two dimensions. The energy modulator 30 and intensity modulator 32 are aligned so that their channels 36 are also aligned.

As will be understood from the following description, either of these modulators 30 and 32 may be used individually as well and/or may also find use for modulation of other types of energy for example x-ray radiation.

The separation of the channels 36 in the energy modulator 30 permits the placement of radio-opaque walls 35 between the channels. The present inventors have determined that the separation of the channels 36 may be controlled so that a natural spreading of the beamlets 24 ensures overlap 38 of the beamlets 24 when they reach the patient. This spreading, and the ability to treat the patient at multiple angles by rotation of the gantry 12, eliminates the problem of the cold spots that would normally be caused by the walls 35. As a result, more sophisticated modulation techniques may be used in areal modulators 30 and 32 than would normally considered feasible.

Figure 3:
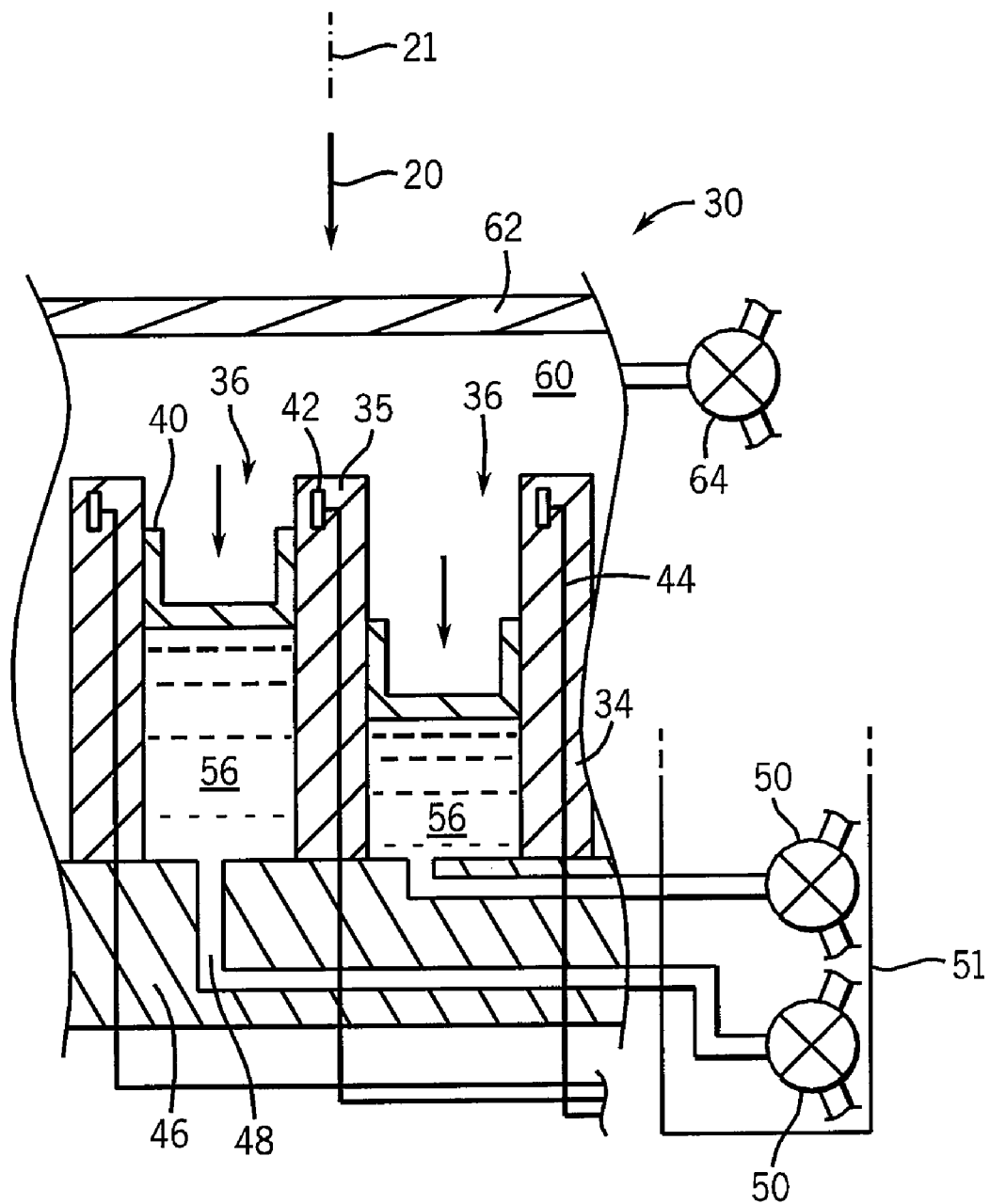
FIG. 3 is a cross-sectional view along line 3-3 of FIG. 2 of the energy modulator employing fluid-filled cylinders that may vary in height to control the energy of the protons.

Referring now to FIG. 3, the energy modulator 30 provides within each of the channels 36 a floating piston 40 that may move axially (along the direction of propagation of the area beam 20). A sensor 42 in the channel walls 35 may provide a signal along line 44 indicating the height of the piston 40 within the channel 36 that may be relayed to a controller 49 executing a stored program 47. For example, the sensor may detect a capacitive change caused by movement of the piston 40 or the material contained by the piston 40.

The lower side of the plate 34 for energy modulator 30 is capped by a radiolucent manifold plate 46 providing a series of conduits 48 leading to each of the channels 36. Each of these conduits 48 may be connected to a valve array 51 including a two-way electrically operable valve 50 associated with each conduit 48 and each channel 36. The valve 50 may connect the conduit 48 to either a high-pressure reservoir 52 or low-pressure reservoir 54 (shown in FIG. 2). The reservoirs may be pressurized by a separate pump system not shown. Each of the valves 50 is connected to and controlled by the controller 49.

A working fluid 56, for example, oil or water may be introduced into each of the channels 36 through the valves 50 from a high-pressure reservoir 52 to fill the channel 36 to a height controlled by feedback sensing of the sensor 42 by the controller 49. Conversely the working fluid 56 may be drawn out of the channels 36 through the valves 50 into the low-pressure reservoir to empty the channel 36 to a height controlled by the feedback sensing of the sensor 42. The height of the column of working fluid 56 is such as at its maximum to wholly block the protons. In this regard 25 cm of water should be sufficient to stop a 200 million electron volt proton.

The upper opening of each channel 36 may be exposed to a common chamber 60 capped by a radiolucent materials 62. This common chamber 60 may be pressurized with another fluid, for example, air through a valve 64 to provide a restoring pressure on each of the pistons 40.

Through the continuous control of the height of the working fluid 56, a continuous control of the energy of protons passing through the channels 36, and hence a location of a Bragg peak of the proton beams within the patient, may be had. Further, the regular geometry of the contained working fluid 56 under the piston 40 (i.e. a cylinder) ensures a consistent energy modification of all protons passing through the channel 36 to provide for precise location of the distal edge of the Bragg peak for all protons.

Figure 4:
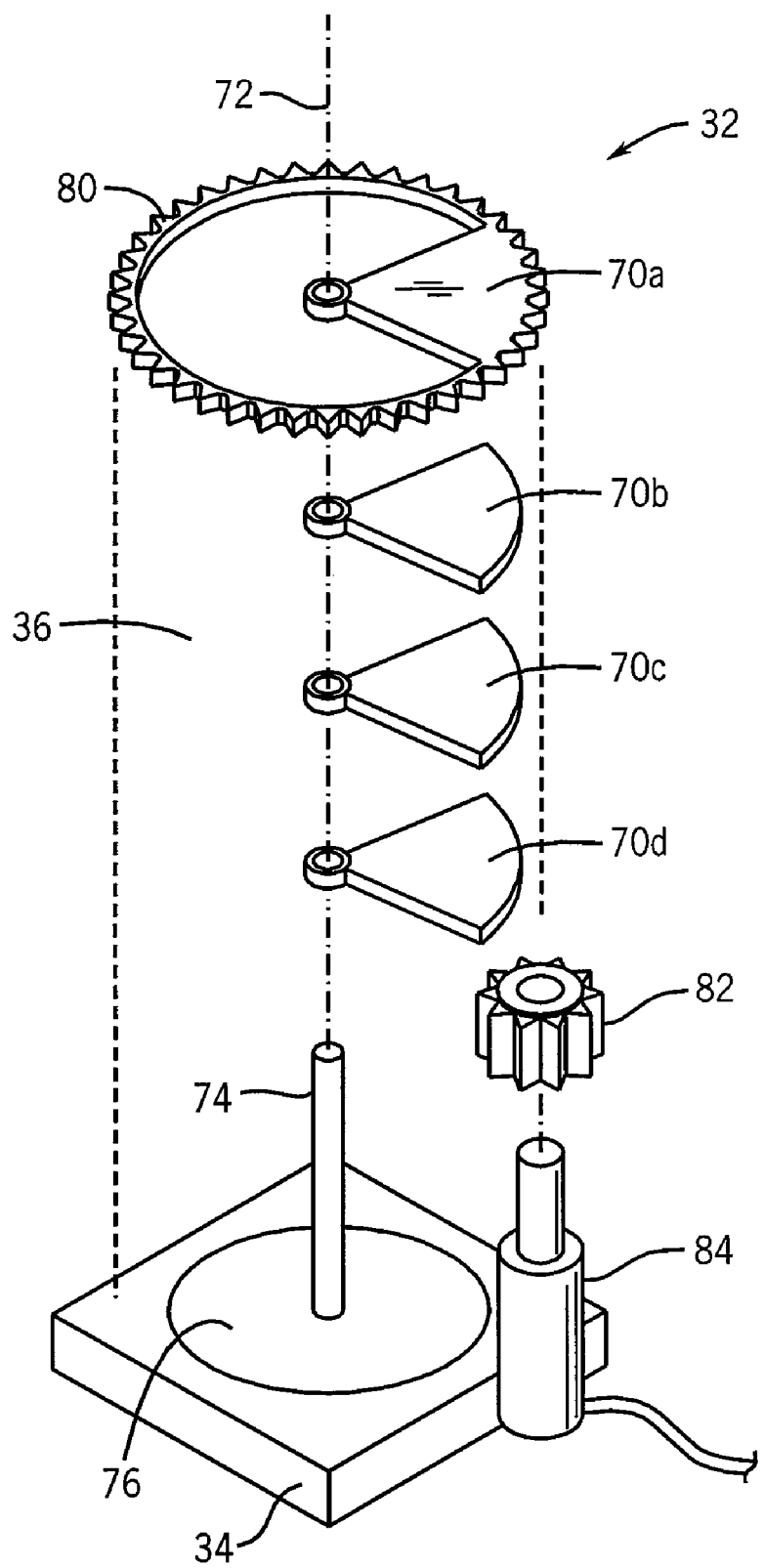
FIG. 4 is an exploded view of mechanical shutter arrangement used for intensity modulation of the areal modulator of FIG. 2 having a set of sector-shaped shutters that may move into and out of alignment.

Referring now to FIGS. 2 and 4, the intensity modulator 32 provides attenuating elements formed of a set of pie-shaped, sector shutters 70a, 70b, 70c, and 70d. The shutters 70 rotate about a common axis 72 aligned with axis 21 of the area beam 20, with each shutter 70 lying and moving within separate but parallel planes with the common axis 72 positioned at the apex of the sector. Only four shutters are shown for clarity, however typically five metal shutters will be provided, each 3 cm thick to be able to individually stop the beam of protons.

Each of the shutters 70 has a bearing on its apex fitting on a radio opaque shaft 74 supported by a radiolucent plug 76 at the bottom of each channel 36 in the plate 34. Each shutter 70 may rotate wholly within the channel 36 and the area outside of the plug 76 is a radio-opaque portion of plate 34.

Referring now also to FIG. 5, the topmost shutter 70a has a peripheral ring gear 80 attached to the outer circumference of the shutter 70a to rotate therewith concentrically about axis 72. Outwardly extending teeth on the ring gear 80 may be engaged by a pinion gear 82 attached to a servomotor or stepper motor 84 controlled by the controller 49. Thus the shutter 70a may be rotated throughout as much as 360°. Each of the remaining shutters 70b, 70c, and 70d are spring-loaded in a counterclockwise direction against a stop (the spring and stop not shown) to remain in alignment with each other and with shutter 70a when the shutter 70a is in a starting position as shown in FIG. 4.

Figure 5A:
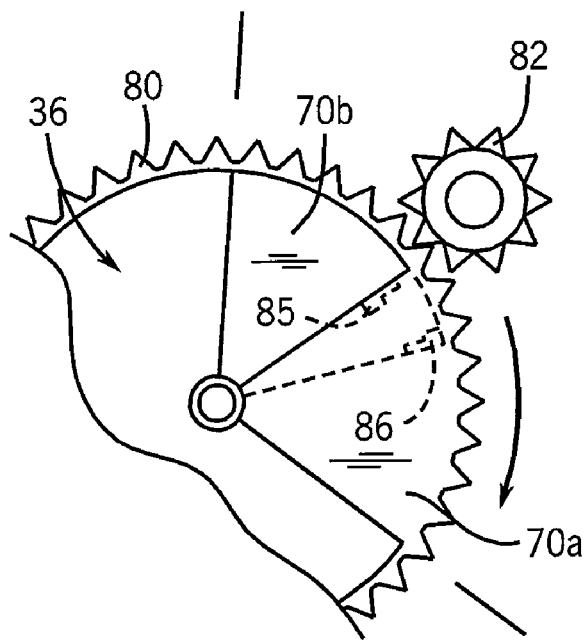
FIGS. 5a and 5b are fragmentary top plan views of the shutters in two states of operation.
Figure 5B:
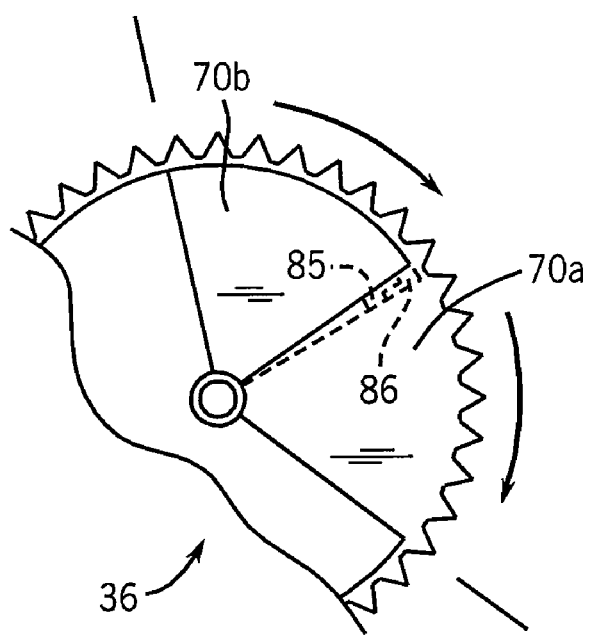

As shown in FIG. 5a, under the influence of the pinion gear 82, shutter 70a may be advanced in a clockwise direction and, as it advances, moved out of overlap with the other shutters 70b-d. As a result, the channel 36 is increasingly blocked by a variable amount determined by the amount of movement of shutter 70a. When shutter 70a has moved sufficiently far (approximately its angular extent), a tooth 85 on the bottom of shutter 70a engages a corresponding tooth 86 on the top of shutter 70b causing additional advancement of shutter 70a to pull the shutter 70b along with it, increasing the amount of blockage of the channel 36 as shown in FIG. 5b.

This process may be continued with the shutters 70 drawing one another along in a train increasingly blocking an area of the channel 36 until rotation connects the next shutter 70 to the train. Ultimately all shutters 70 are fully extended like a fan and the channel 36 may be fully blocked.

It will be understood that other similar shutter arrangements may be used including those emulating an iris of a typical camera or those that have pinwheel type sector configurations or other arbitrary patterns that may move into and out of alignment with rotation.

The motor 84 may be positioned within the opaque area of the plate 34 thus allowing individual control of the beamlets 24 through each channel 36.

The ability to separately modulate intensity and energy over an area provides for extremely rapid treatment of an area of a patient. This control may be done during rotation of the gantry to provide for sophisticated treatment patterns per the above cited patent and/or analogous to those described in U.S. Pat. Nos. 5,724,400, entitled: "Radiation Therapy System With Constrained Rotational Freedom" and 6,560,311 entitled: "Method For Preparing A Radiation Therapy Plan Related To X-Ray Radiation Therapy" hereby incorporated by reference. At each point in the orbit 16 (shown in FIG. 1) the energy may be modulated to spread the Bragg peak as desired allowing control not only of the depth of the Bragg peak but its width and its intensity for even more precise radiation treatment.

The invention could also work with photons. The area beam 20 may be a cone beam or pyramidal beam. As used herein, attenuation refers generally to both reduction in energy and reduction in intensity, with a particular meaning being evident from context.

It is specifically intended that the present invention not be limited to the embodiments and illustrations contained herein and the claims should be understood to include modified forms of those embodiments including portions of the embodiments and combinations of elements of different embodiments as come within the scope of the following claims.

We claim:

1. A radiation therapy machine comprising:
   a patient support;
   a source of a proton radiation providing an area beam directed toward a patient on the patient support to expose tissue of the patient,
   an areal modulator positioned between the source of proton radiation and the patient support providing:
   (i) a radio-opaque plate extending over an area of the area beam and having a plurality of channels dispersed in two dimensions within the area for passing proton radiation, each channel being separated from adjacent channels by an associated portion of the radio-opaque plate bordering the channels, and the associated portion of the radio-opaque plate blacking passage of the proton radiation;
   (ii) adjustable intensity attenuation elements located in each of the channels to independently attenuate the intensity of proton radiation passing through the channels, wherein each adjustable intensity attenuation element is disposed wholly within an area defined by the channel and the associated portion of the radio-opaque plate bordering the channel;
   wherein the intensity attenuation elements provide a variable blocking of the channels to vary the intensity of the proton radiation passing through the channels;
   (iii) energy attenuation elements located in each of the channels to independently attenuate the energy of proton radiation passing through the channels;
   wherein the energy attenuation elements include an opening extending along an axis of the channels to hold attenuating fluid and connected to at least one valve system configured to adjust a height of a floating piston defining a boundary between the attenuating fluid and a second non-attenuating fluid disposed within each attenuation opening, the floating piston configured to move and adjust the height of attenuating fluid along the axis to concurrently vary the energy of the proton radiation passing through multiple channels and maintain a fluid level in response to rotational movement of the channels about the patient support, and
   wherein the channels are spaced with respect to each other so that divergence of the proton radiation after passing through the radio-opaque plate overlaps to permit substantially contiguous exposure of the tissue of the patient over an area corresponding to the area of the channels and the area of the portion of the radio-opaque plate bordering the channels at a given gantry angle.

2. The radiation therapy machine of claim 1 disposed within a gantry that is moved through a plurality of gantry angles during a radiation therapy session, and further including a controller that independently controls the attenuation through each of the channels as a function of gantry angle.

3. The radiation therapy machine of claim 1 wherein the proton attenuating fluid is selected from the group consisting of oil and water.

4. The radiation therapy machine of claim 1 wherein each opening connects to at least two valves one connected to a high-pressure reservoir to fill the opening and one connected to a low-pressure reservoir to empty the opening.

5. The radiation therapy machine of claim 1 further including sensors for sensing the height of the piston and providing an electrical signal to a control system for regulating the height of the attenuating fluid in the opening.

6. The radiation therapy machine of claim 1 disposed within a gantry that is moved through a plurality of gantry angles during a radiation therapy session, and further including a controller that controls the height of the attenuating fluid along the axis to vary continuously as a function of gantry angle.

7. The radiation therapy machine of claim 1 wherein the intensity attenuation elements comprise shutters that variably block the channels by changing an amount of overlap between different shutter elements.

8. The radiation therapy machine of claim 1 wherein the shutters are disks rotating about a common axis centered within the channel having cutouts that move into and out of alignment with rotation of the disks.

9. The radiation therapy machine of claim 1 wherein the energy and intensity of the area beam is modified within a two-dimensional area correlating to a target tissue of the patient.

10. The radiation therapy machine of claim 1 wherein the energy attenuation elements located in each of the channels independently attenuates the range the proton radiation passing through the channels, and wherein the intensity attenuation elements located within either the channel or the associated portion of the radio-opaque plate bordering the channel independently attenuates the intensity the proton radiation passing through the channels.

11. A method of radiation therapy comprising:
   (a) supporting a patient on a patient support to receive an area beam of proton radiation directed to the patient from a radiation source,
   (b) positioning an areal modulator between the source of proton radiation and the patient support where in the areal modulator extends over an area of the beam and has a plurality of channels, having circular cross sections, within the area for passing proton radiation, each channel being separated from adjacent channels by an associated portion of the area modulator bordering the channels, the portion of the area modulator bordering the channels blocking passage of the proton radiation;
   (c) controlling first energy attenuation elements of each of the channels
   to independently and concurrently control the energy of the proton radiation passing through various channels;
   (d) controlling second adjustable intensity attenuation elements of each of the channels to independently control the intensity of the proton radiation passing through the channels, each second adjustable intensity attenuation element disposed wholly within an area defined by the channel and the associated portion of the radio-opaque plate bordering the channel;
   wherein the channels are spaced with respect to each other so that divergence of the proton radiation after passing through the areal modulator overlaps to permits substantially contiguous exposure of the patient over an area corresponding to the area of the channels and the area of the portion of the areal modulator bordering the channels, when the area beam is at a given gantry angle.

12. The method of claim 11 where in the areal modulator is disposed within a gantry and further including the steps of moving the gantry through a plurality of gantry angles while independently controlling the attenuation through each of the channels as a function of gantry angle.

13. The method of claim 11 wherein the first attenuation elements are cylinders extending along an axis of the channels to hold attenuating fluid and including the step of adjusting a height of attenuating fluid along the axis to continuously vary the energy fluence of radiation passing through the channels.

14. The method of claim 13 wherein the attenuating fluid is selected from the group consisting of oil and water.

15. The method of claim 13 wherein each cylinder connects to at least two valves, one connected to a high-pressure reservoir and one connected to a low-pressure reservoir and including the step of changing a connection of the cylinder between the reservoirs to control the height of the fluid in the cylinder.

16. The method of claim 13 further including the step of sensing the height of the fluid in the cylinder to control the height of the fluid in the cylinder.

17. The method of claim 13 wherein the areal modulator is disposed within a gantry and including the step of moving the gantry through a plurality of gantry angles during a radiation therapy session while controlling the height of the attenuating fluid along the axis to vary continuously as a function of gantry angle.

18. The method of claim 11 wherein the second attenuation elements are shutters and including the step of moving the shutters to provide a continuously variable blocking of the channels to control the intensity of the proton radiation passing through the channels.

19. The method of claim 18 wherein the shutters variably block the channels by changing an amount of overlap between different shutter elements in both modulation systems.

\* \* \* \* \*